US010007763B2

(12) United States Patent
Takamatsu

(10) Patent No.: US 10,007,763 B2
(45) Date of Patent: Jun. 26, 2018

(54) DRUG PRESCRIBING SYSTEM

(71) Applicant: TAKAZONO TECHNOLOGY INCORPORATED, Hirakata-shi, Osaka (JP)

(72) Inventor: Akira Takamatsu, Hirakata (JP)

(73) Assignee: TAKAZONO TECHNOLOGY INCORPORATED, Hirakata-shi (JP)

(*) Notice: Subject to any disclaimer, the term of this patent is extended or adjusted under 35 U.S.C. 154(b) by 553 days.

(21) Appl. No.: 14/391,375

(22) PCT Filed: Apr. 19, 2013

(86) PCT No.: PCT/JP2013/061601
§ 371 (c)(1),
(2) Date: Oct. 8, 2014

(87) PCT Pub. No.: WO2013/161694
PCT Pub. Date: Oct. 31, 2013

(65) Prior Publication Data
US 2015/0073819 A1 Mar. 12, 2015

(30) Foreign Application Priority Data
Apr. 24, 2012 (JP) ................... 2012-098648

(51) Int. Cl.
*G06F 19/00* (2018.01)
*G06Q 50/22* (2018.01)
(52) U.S. Cl.
CPC ...... *G06F 19/3456* (2013.01); *G06F 19/3462* (2013.01); *G06Q 50/22* (2013.01)
(58) Field of Classification Search
CPC .... G06F 19/3456; G16H 20/10; G16H 20/60; G16H 20/70; G16H 20/90
See application file for complete search history.

(56) References Cited

U.S. PATENT DOCUMENTS

2011/0168733 A1 7/2011 Yuyama et al.
2013/0110282 A1* 5/2013 Omura ............... G07F 17/0092
700/233

FOREIGN PATENT DOCUMENTS

CN 1661618 A 8/2005
CN 102159172 A 8/2011
(Continued)

OTHER PUBLICATIONS

European Search Report dated Nov. 17, 2015 issued in counterpart application No. PCT/JP2013-061601, with English translation (7 pages).
(Continued)

*Primary Examiner* — Linh Giang Le
(74) *Attorney, Agent, or Firm* — Westerman, Hattori, Daniels & Adrian, LLP

(57) ABSTRACT

A drug prescribing system that can prevent a wrong drug from being taken during picking is provided. A drug prescribing system includes a host computer including an input device through which prescription data based on a prescription is input, a drug dispensing apparatus in which drugs are housed in advance, and that dispenses a drug in accordance with the prescription data, and a picking inspection apparatus that conducts a picking inspection for a drug picked in accordance with the prescription data. The drug dispensing apparatus outputs supplementary information on a drug that is not dispensed with the drug dispensing apparatus and needs to be supplemented. The picking inspection apparatus receives an input of the supplementary information, and conducts the picking inspection for a supplementary drug supplemented based on the supplementary information.

7 Claims, 9 Drawing Sheets

(56) References Cited

FOREIGN PATENT DOCUMENTS

| JP | 07-220011 A | 8/1995 |
|---|---|---|
| JP | 9-192201 A | 7/1997 |
| JP | 2000-276551 A | 10/2000 |
| JP | 2002-236748 A | 8/2002 |
| JP | 2004-157579 A | 6/2004 |
| JP | 2004-216144 A | 8/2004 |
| JP | 2006-81837 A | 3/2006 |
| JP | 2006-247150 A | 9/2006 |
| JP | 2008-93177 A | 4/2008 |
| JP | 2011-41789 A | 3/2011 |
| JP | 2012-16461 A | 1/2012 |
| WO | 2010/032479 A1 | 3/2010 |
| WO | 2012005039 A1 | 1/2012 |

OTHER PUBLICATIONS

European Search Report dated Nov. 17, 2015, issued in counterpart European Patent Application No. 13781177.4, with English translation. (7 pages).
International Search Report dated Jul. 30, 2013 issued in application No. PCT/JP2013/061601.
Office Action dated Apr. 25, 2017, issued in counterpart Japanese Patent Application No. 2016-165651, with English translation. (8 pages).
Office Action dated Feb. 6, 2017, issued in counterpart Chinese Application No. 201380021887.6, with English translation (15 pages).

* cited by examiner

DRUG PRESCRIBING SYSTEM

TECHNICAL FIELD

The present invention relates to a drug prescribing system, and particularly to a drug prescribing system including a drug dispensing apparatus and a picking inspection apparatus.

BACKGROUND ART

Drugs are prescribed in accordance with a doctor's prescription at a pharmacy in a hospital, for example. In prescribing drugs, a pharmacist collects appropriate quantities of predetermined types of drugs in accordance with the prescription. This work is referred to as "picking".

A system related to picking has previously been proposed, in which a marking on work instructions formed by encoding the articles to be picked, the quantities of the articles, the order of picking, and the like is read with a mobile terminal, and the articles written on the work instructions are accurately collected (see, for example, Japanese Patent Laying-Open No. 2000-276551 (PTD 1)). Another system has been proposed in which drug prescription data based on a prescription is transferred to a mobile terminal from a computer, and a bar code of drugs read with the mobile terminal is compared with a bar code in the drug prescription data (see, for example, Japanese Patent Laying-Open No. 2002-236748 (PTD 2)). A yet another system has been proposed in which an appropriate inspection is conducted by comparing prescription data for picking inspection that has undergone a picking inspection, which is transmitted from a mobile terminal, with prescription data for picking inspection created based on the prescription data (see, for example, Japanese Patent Laying-Open No. 2006-81837 (PTD 3)).

Meanwhile, an apparatus for automatically collecting predetermined quantities of predetermined drugs based on a preset program has been proposed. Japanese Patent Laying-Open No. 2008-93177 (PTD 4), for example, discloses a drug prescribing apparatus including a sheet-heading mechanism for improving the efficiency of taking out PTP (Press Through Package) sheets packed with tablets.

Since there are several hundreds of types of drugs used at a pharmacy, it is difficult to automatically collect all these drugs stored in an apparatus. At present, therefore, drugs that are used with relatively high frequency are automatically collected, while other drugs are picked from a drug shelf, and a required set of drugs are collected by combining both these drugs. Japanese Patent Laying-Open No. 9-192201 (PTD 5) proposes an ampoule collecting method related to such work. In this method, an ampoule dispensing apparatus for automatically collecting ampoules outputs a list of ampoules based on a prescription. The list shows in emphasis drugs that could not be dispensed with the ampoule dispensing apparatus. The ampoules are then manually collected from the shelf in accordance with the list.

CITATION LIST

Patent Document

PTD 1: Japanese Patent Laying-Open No. 2000-276551
PTD 2: Japanese Patent Laying-Open No. 2002-236748
PTD 3: Japanese Patent Laying-Open No. 2006-81837
PTD 4: Japanese Patent Laying-Open No. 2008-93177
PTD 5: Japanese Patent Laying-Open No. 9-192201

SUMMARY OF INVENTION

Technical Problem

With the technique according to Japanese Patent Laying-Open No. 9-192201 (PTD 5), a worker needs to pick those ampoules that could not be dispensed with the ampoule dispensing apparatus after the ampoules are dispensed with the ampoule dispensing apparatus. Collecting all the ampoules thus takes time. Moreover, the worker may take a wrong drug during picking of ampoules.

The present invention was made in view of the above-described problems, and a main object is to provide a drug prescribing system that can reduce the time required to collect drugs, and prevent a worker from taking a wrong drug during picking of drugs.

Solution to Problem

A drug prescribing system according to the present invention includes a prescription data input device through which prescription data based on a prescription is input, a drug dispensing apparatus in which drugs are housed in advance, and that dispenses a drug in accordance with the prescription data, and a picking inspection apparatus that conducts a picking inspection for a drug picked in accordance with the prescription data. The drug dispensing apparatus outputs supplementary information on a drug that is not dispensed with the drug dispensing apparatus and needs to be supplemented. The picking inspection apparatus receives an input of the supplementary information, and conducts the picking inspection for a supplementary drug supplemented based on the supplementary information.

Preferably, in the drug prescribing system, the drug dispensing apparatus prints a dispensation result slip; the picking inspection apparatus has a bar code reader capable of reading a bar code, and conducts the picking inspection by reading a bar code provided for a drug through the bar code reader; the supplementary information is barcoded and printed on the dispensation result slip; and the bar code reader reads a bar code printed on the dispensation result slip, which causes the supplementary information to be transmitted from the drug dispensing apparatus to the picking inspection apparatus.

Preferably, the drug prescribing system further includes a storage device that stores a dispensation record on dispensation of the drug with the drug dispensing apparatus, and a picking record on the picking inspection by the picking inspection apparatus, wherein the supplementary drug is included in the picking record, and not included in the dispensation record.

Advantageous Effects of Invention

The drug prescribing system of the present invention can reduce the time required to collect drugs, and prevent a worker from taking a wrong drug during picking of drugs.

DESCRIPTION OF EMBODIMENTS

Embodiments of this invention will be described hereinafter, with reference to the drawings. In the following drawings, identical or corresponding parts are indicated with identical reference numbers, and description thereof will not be repeated.

(First Embodiment)

Figure 1:
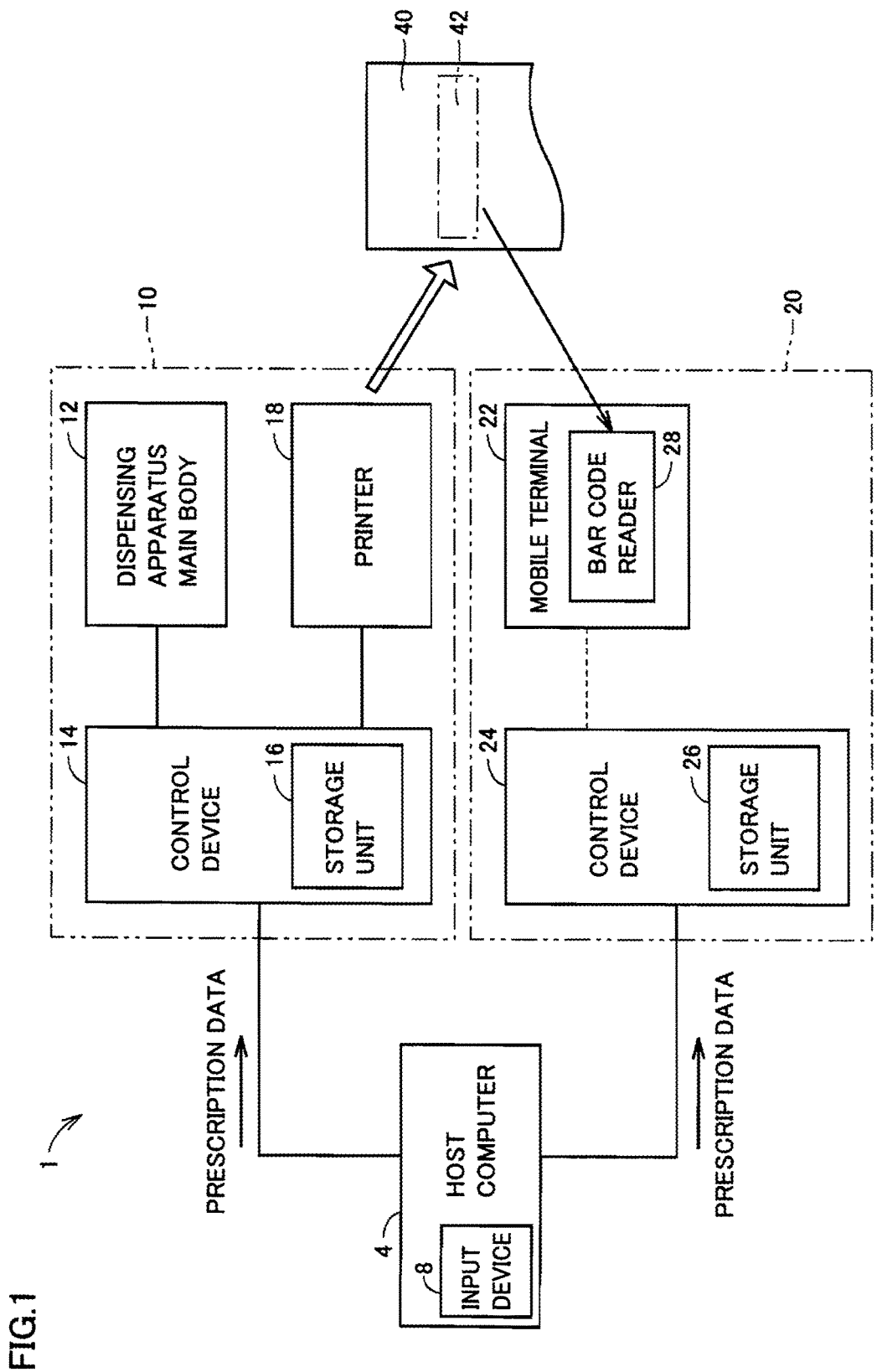
FIG. 1 is a block diagram illustrating the schematic configuration of a drug prescribing system according to a first embodiment.

FIG. 1 is a block diagram illustrating the schematic configuration of a drug prescribing system 1 according to a first embodiment. As shown in FIG. 1, drug prescribing system 1 includes a host computer 4, a drug dispensing apparatus 10, and a picking inspection apparatus 20.

Host computer 4 includes an input device 8. Prescription data based on a prescription prepared by a doctor is input to host computer 4 with input device 8. The prescription data includes prescription identification information, patient information, and prescription information. The prescription identification information corresponds to a reception number of the prescription. The patient information includes a patient ID and the patient's name. The prescription information includes the names, uses, and doses of drugs. Host computer 4 transmits the prescription data to drug dispensing apparatus 10 and picking inspection apparatus 20 simultaneously.

Drug dispensing apparatus 10 serves to automate picking, and prevent a wrong drug from being prescribed. Drug dispensing apparatus 10 dispenses a prescribed dose of a predetermined type of a drug, in accordance with the prescription data transmitted from host computer 4. Drug dispensing apparatus 10 includes a dispensing apparatus main body 12, a control device 14, and a printer 18. Various drugs are housed in advance in dispensing apparatus main body 12.

Control device 14 controls dispensing apparatus main body 12 to dispense a required number of drugs to be dispensed, based on the prescription data transmitted from host computer 4. Control device 14 also controls printer 18 to print a dispensation result slip 40. Control device 14 includes a storage unit 16. Storage unit 16 stores drug master data. The drug master data includes pieces of information such as information on whether the drugs included in the prescription data are drugs to be dispensed with drug dispensing apparatus 10 or not, information on the number of drugs per box, and the like. Storage unit 16 also stores a dispensation record on the dispensation of drugs with drug dispensing apparatus 10.

Printer 18 prints dispensation result slip 40 based on a result of the dispensation of drugs from dispensing apparatus main body 12. A bar code 42 is printed on dispensation result slip 40. Supplementary information on a drug that has not been dispensed from drug dispensing apparatus 10 and needs to be supplemented is barcoded and output as bar code 42. The supplementary information includes a drug code of the supplementary drug. The supplementary information may also include a quantity of the supplementary drug to be supplemented.

Picking inspection apparatus 20 serves to check whether a worker has not picked a wrong drug. Picking inspection apparatus 20 conducts a picking inspection for the drug picked in accordance with the prescription data transmitted from host computer 4. As referred to herein, the teiin "picking inspection" means checking whether any wrong drug has not been taken by a worker during picking of drugs, and the types and the quantities of drugs as prescribed in the prescription have been collected. Picking inspection apparatus 20 includes a mobile terminal 22 and a control device 24.

Mobile terminal 22 has a bar code reader 28 for reading a bar code. Mobile terminal 22 reads the bar code provided for a drug, through bar code reader 28. The bar code is provided on a drug shelf in which drugs are housed. The bar code may be provided on a pharmaceutical package (a PTP sheet, for example), or may be provided on a sales package (a box housing a plurality of PTP sheets, for example). A check to find whether any wrong drug has not been taken, i.e., a picking inspection, is conducted by comparing the drug indicated with the bar code that has been read through bar code reader 28 during picking, with the drug indicated in the prescription data transmitted from host computer 4.

Mobile terminal 22 also reads bar code 42 printed on dispensation result slip 40, and receives an input of the supplementary information on the drug that needs to be supplemented. Bar code reader 28 reads bar code 42, causing the supplementary information on the drug that needs to be supplemented to be transmitted to picking inspection apparatus 20 from drug dispensing apparatus 10. When the worker conducted additional picking based on the supplementary information input through reading of bar code 42, picking inspection apparatus 20 conducts an additional picking inspection for the supplementary drug supplemented based on the supplementary information. That is, the additional picking inspection is conducted by comparing the drug indicated with the bar code read with mobile terminal 22 during the additional picking, with the drug recognized as the supplementary drug through reading of bar code 42.

Control device 24 transmits, via wireless LAN, picking instruction data based on the prescription data to mobile terminal 22, and receives picking result data from mobile terminal 22. Control device 24 has a storage unit 26. Storage unit 26 stores the drug master data. The drug master data includes pieces of information such as information on whether the drugs included in the prescription data are drugs to be picked by the worker or not, and the like. Storage unit 26 also stores a picking record on the picking inspection conducted by picking inspection apparatus 20.

Figure 2:
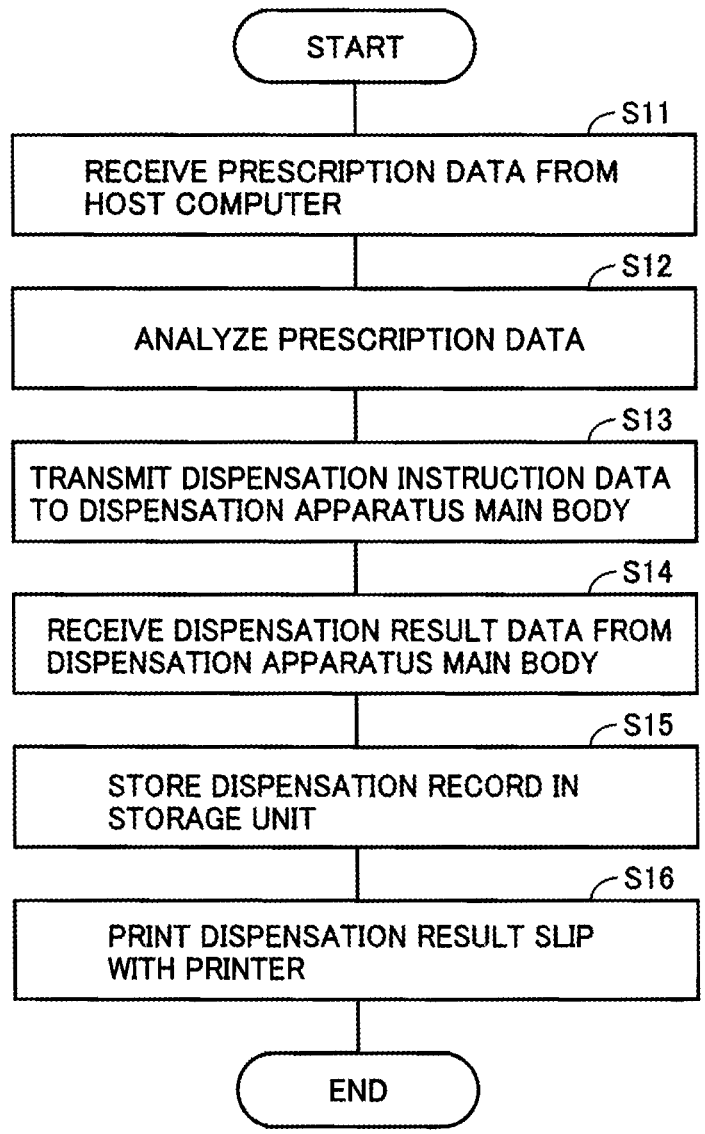
FIG. 2 is a flowchart illustrating the operation of a control device of a drug dispensing apparatus.

FIG. 2 is a flowchart illustrating the operation of control device 14 of drug dispensing apparatus 10. Control device 14 of drug dispensing apparatus 10 controls drug dispensing apparatus 10 in accordance with the steps shown in FIG. 2. With reference to FIG. 2, the operation of control device 14 of drug dispensing apparatus 10 will be described in detail.

As shown in FIG. 2, control device 14 receives the prescription data from host computer 4 in step (S11), and analyzes the received prescription data in step (S12). Control device 14 compares the drugs included in the prescription data with the drug master data stored in storage unit 16, and analyzes whether the drugs included in the prescription data are drugs to be dispensed with drug dispensing apparatus 10 or not, based on the compared result. On the basis of the analyzed result, control device 14 recognizes drugs to be dispensed with drug dispensing apparatus 10 among the drugs included in the prescription data.

Then in step (S13), control device 14 transmits dispensation instruction data to dispensing apparatus main body 12 for instructing it to dispense a prescribed dose of a drug to be dispensed. Dispensing apparatus main body 12 that has received the dispensation instruction data dispenses the drug to be dispensed, and transmits dispensation result data indicating the dispensation result.

Control device 14 receives the dispensation result data from dispensing apparatus main body 12 in step (S14). As used herein, the dispensation result data transmitted from dispensing apparatus main body 12 to control device 14 indicates the types and the quantities of drugs actually dispensed from dispensing apparatus main body 12. That is, the dispensation result data excludes information on a drug that was included as a drug to be dispensed but was not actually dispensed from dispensing apparatus main body 12.

Control device 14 then causes a dispensation record based on the dispensation result data to be stored in storage unit 16 in step (S15). The dispensation record does not include the information on a drug that was included as a drug to be dispensed but was not actually dispensed from dispensing apparatus main body 12. Control device 14 also prints dispensation result slip 40 with printer 18 in step (S16). Dispensation result slip 40 will be described in detail below.

Figure 3:
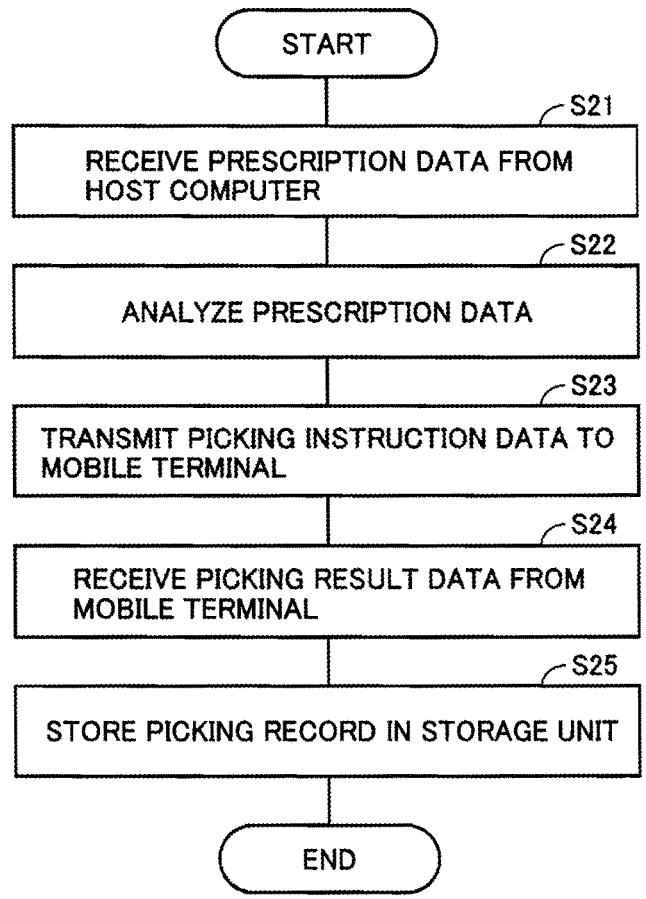
FIG. 3 is a flowchart illustrating the operation of a control device of a picking inspection apparatus.
Figure 4:
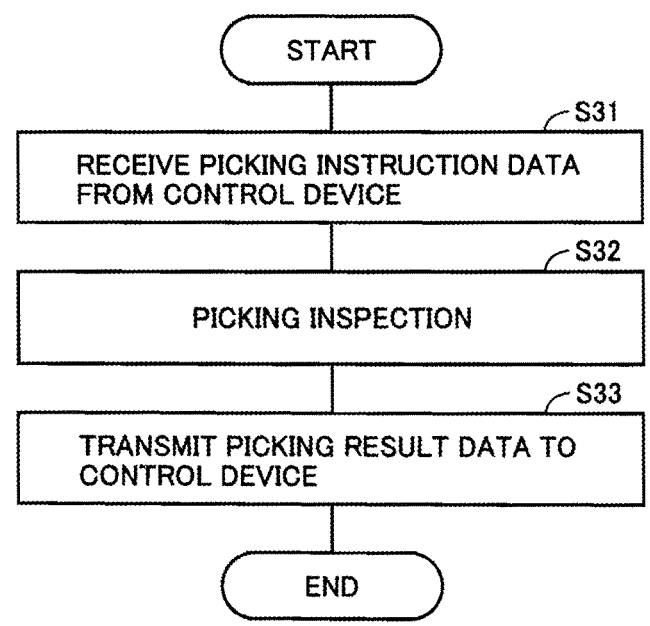
FIG. 4 is a flowchart illustrating the operation of a mobile terminal of the picking inspection apparatus.

FIG. 3 is a flowchart illustrating the operation of control device 24 of picking inspection apparatus 20. Control device 24 of picking inspection apparatus 20 operates in accordance with the steps shown in FIG. 3. FIG. 4 is a flowchart illustrating the operation of mobile terminal 22 of picking inspection apparatus 20. Mobile terminal 22 of picking inspection apparatus 20 operates in accordance with the steps shown in FIG. 4. With reference to FIGS. 3 and 4, the operation of control device 24 and mobile terminal 22 of picking inspection apparatus 20 will be described in detail.

As shown in FIG. 3, control device 24 receives the prescription data from host computer 4 in step (S21), and analyzes the received prescription data in step (S22). Control device 24 compares the drugs included in the prescription data with the drug master data stored in storage unit 26, and analyzes whether the drugs included in the prescription data are drugs to be picked by the worker or not, based on the compared result. Control device 24 recognizes, as drugs to be picked, drugs not included as drugs to be dispensed with drug dispensing apparatus 10 among the drugs included in the prescription data. On the basis of the analyzed result, control device 24 recognizes drugs to be picked by the worker among the drugs included in the prescription data. Then in step (S23), control device 24 transmits, via wireless LAN, the picking instruction data indicating the prescription information of the drugs to be picked, to mobile terminal 22.

In step (S31) shown in FIG. 4, mobile terminal 22 receives the picking instruction data transmitted from control device 24 of picking inspection apparatus 20 in step (S23). Mobile terminal 22 that has received the picking instruction data displays the drugs to be picked on the screen. The worker conducts picking while checking the drugs to be picked with reference to the screen on mobile terminal 22, and conducts a picking inspection through reading of the bar code indicating the drugs to be picked (step (S32)). After the completion of the picking inspection, mobile terminal 22 transmits the picking result data indicating the result of picking inspection to control device 24 (step (S33)).

Returning to FIG. 3, control device 24 of picking inspection apparatus 20 receives the picking result data from mobile terminal 22 in step (S24). Control device 24 then causes the picking record based on the picking result data to be stored in storage unit 26 in step (S25).

The worker checks dispensation result slip 40 output from drug dispensing apparatus 10 when he/she collects the drugs dispensed with drug dispensing apparatus 10 and the drugs picked from the pharmaceutical shelf The prescription of drugs is completed if all the drugs to be dispensed have been dispensed with drug dispensing apparatus 10 as a result of the dispensation. If any drug to be dispensed has not been dispensed with drug dispensing apparatus 10, additional picking will be required, as will be described below. The worker collects the drug that could not be dispensed from drug dispensing apparatus 10 by picking it again, based on the supplementary information indicated in dispensation result slip 40.

Figure 5:
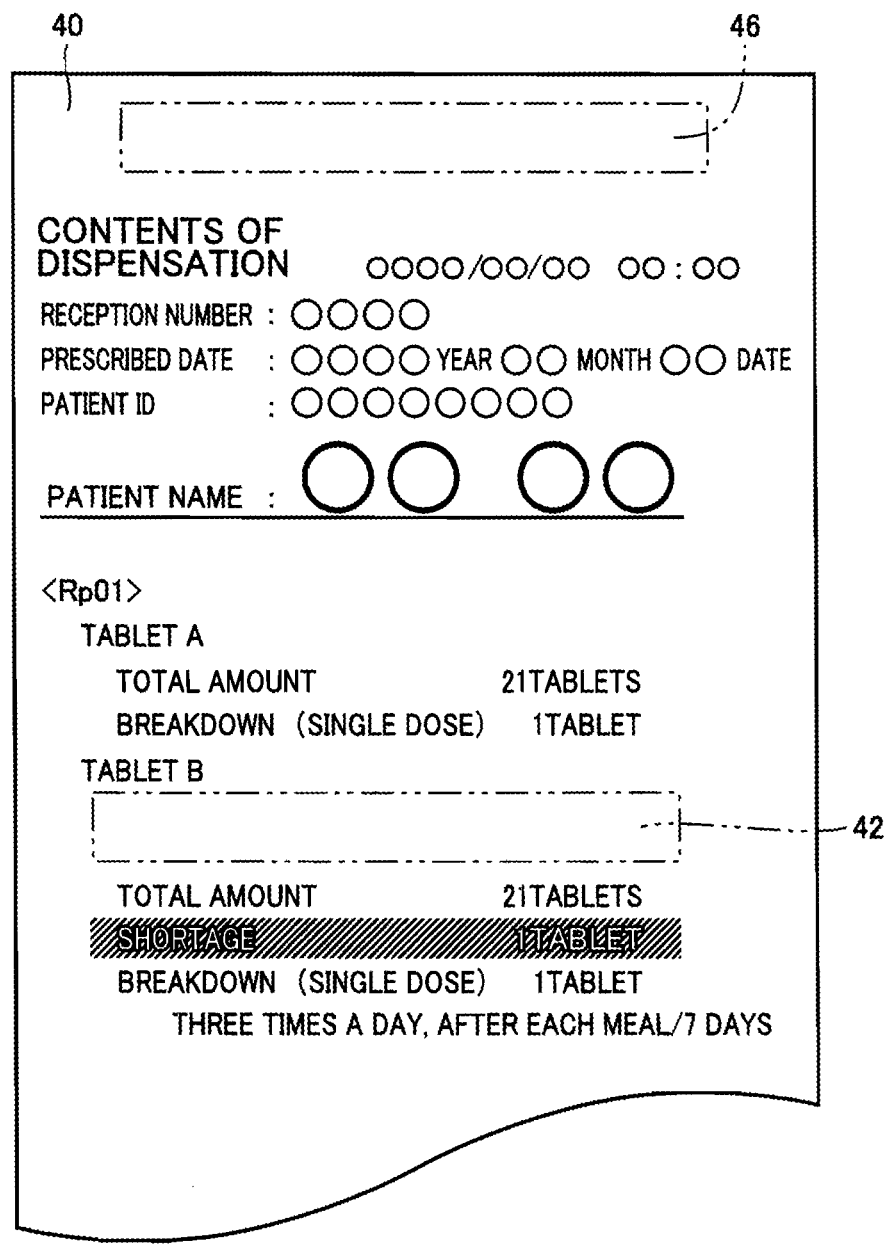
FIG. 5 is a schematic diagram illustrating a first example of a dispensation result slip output by the drug dispensing apparatus.

FIG. 5 is a schematic diagram illustrating a first example of dispensation result slip 40 output by drug dispensing apparatus 10. Detailed contents of the dispensation of the drugs dispensed with drug dispensing apparatus 10 are printed on dispensation result slip 40. Specifically, as shown in FIG. 5, the date and the time of the dispensation of the drugs from drug dispensing apparatus 10, the reception number of the prescription, the prescribed date, the patient ID, and the patient name are printed on dispensation result slip 40. The reception number of the prescription is barcoded and printed on dispensation result slip 40 as bar code 46. The names of the drugs dispensed with drug dispensing apparatus 10, and the total amount and the single dose for each prescribed drug are also printed on dispensation result slip 40.

The print on dispensation result slip 40 shown in FIG. 5 indicates that a total of 21 tablets A, which are taken one tablet at a time, were dispensed. The required amount of tablets A were all dispensed from drug dispensing apparatus 10, and thus, the worker need not pick any additional tablet A. The print on dispensation result slip 40, on the other hand, indicates that there is a shortage of one tablet for tablets B, which are taken one tablet at a time. That is, although it was necessary to dispense a total of 21 tablets B according to the prescription, the number of tablets B housed in drug dispensing apparatus 10 was insufficient. The print on dispensation result slip 40 thus indicates that 20 tablets B were dispensed from drug dispensing apparatus 10, with a shortage of one tablet B as a result of the dispensation.

The drug code and the number of insufficient tablet B that was not dispensed are barcoded and printed on dispensation result slip 40 as bar code 42. The supplementary information indicated with bar code 42 is read with mobile terminal 22 of picking inspection apparatus 20, and the worker collects the insufficient drug by picking it from the pharmaceutical shelf based on the supplementary information. Bar code 42 corresponding to the drug that needs to be supplemented by the worker is printed on dispensation result slip 40. The bar code, however, does not include information on drugs that need not be supplemented by the worker.

Figure 6:
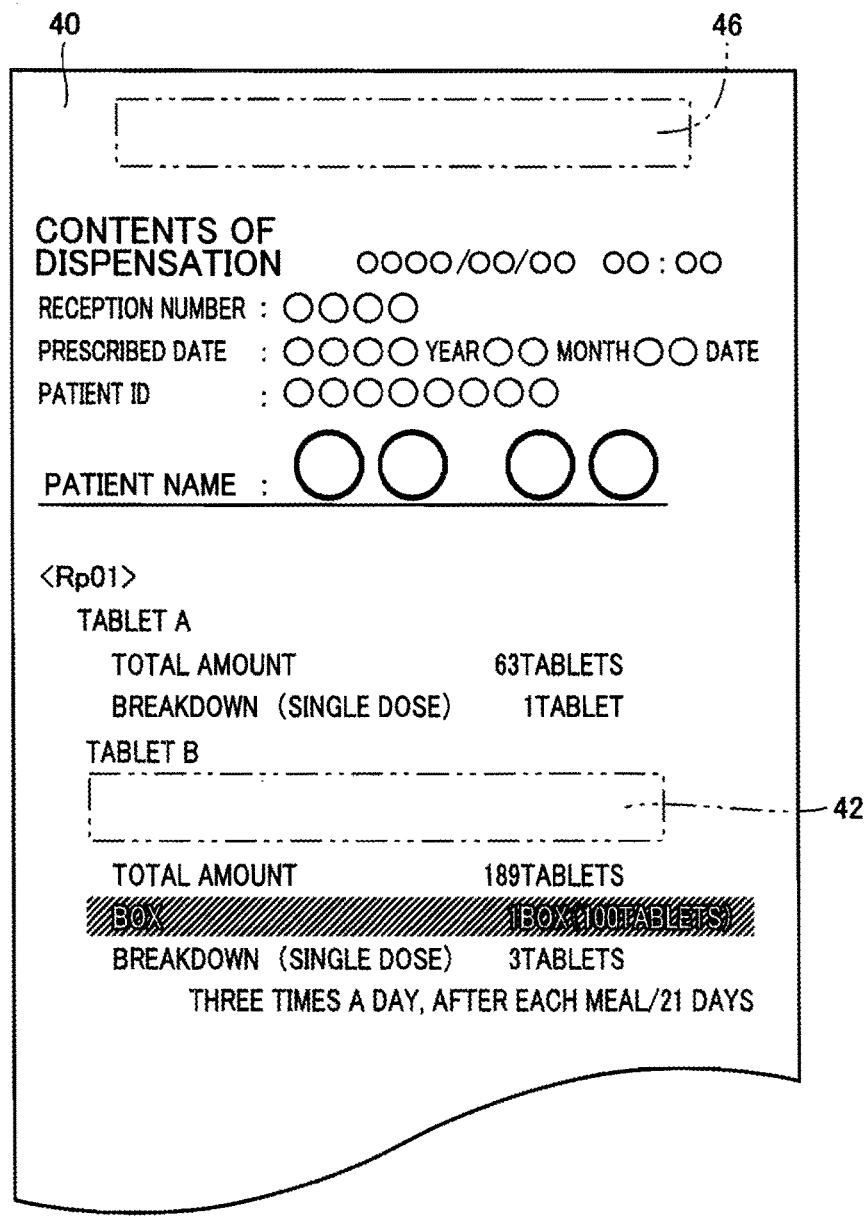
FIG. 6 is a schematic diagram illustrating a second example of the dispensation result slip output by the drug dispensing apparatus.

FIG. 6 is a schematic diagram illustrating a second example of dispensation result slip 40 output by drug dispensing apparatus 10. The print on dispensation result slip 40 shown in FIG. 6 indicates that a total of 63 tablets A, which are taken one tablet at a time, were dispensed. The required amount of tablets A were all dispensed from drug dispensing apparatus 10, and thus, the worker need not pick any additional tablet A.

The print on dispensation result slip 40, on the other hand, indicates that one box (100 tablets) of tablets B, which are taken three tablets at a time, were not dispensed. That is, when the amount of required tablets B in accordance with the prescription is equal to or more than the number of tablets B per box, the worker can prepare tablets B more quickly by picking them in a box. The print on dispensation result slip 40 thus indicates that drug dispensing apparatus 10 dispensed 89 tablets B, which is the remainder of the result of dividing the required number by the number of tablets per box, but did not dispense the number of tablets B corresponding to one box as a result of the dispensation.

The drug code and the insufficient number of tablets B that need to be picked in a box are barcoded and printed on dispensation result slip 40 as bar code 42. The supplementary information indicated with bar code 42 is read with mobile terminal 22 of picking inspection apparatus 20, and the worker collects the insufficient drug by picking it from the pharmaceutical shelf based on the supplementary information.

Figure 7:
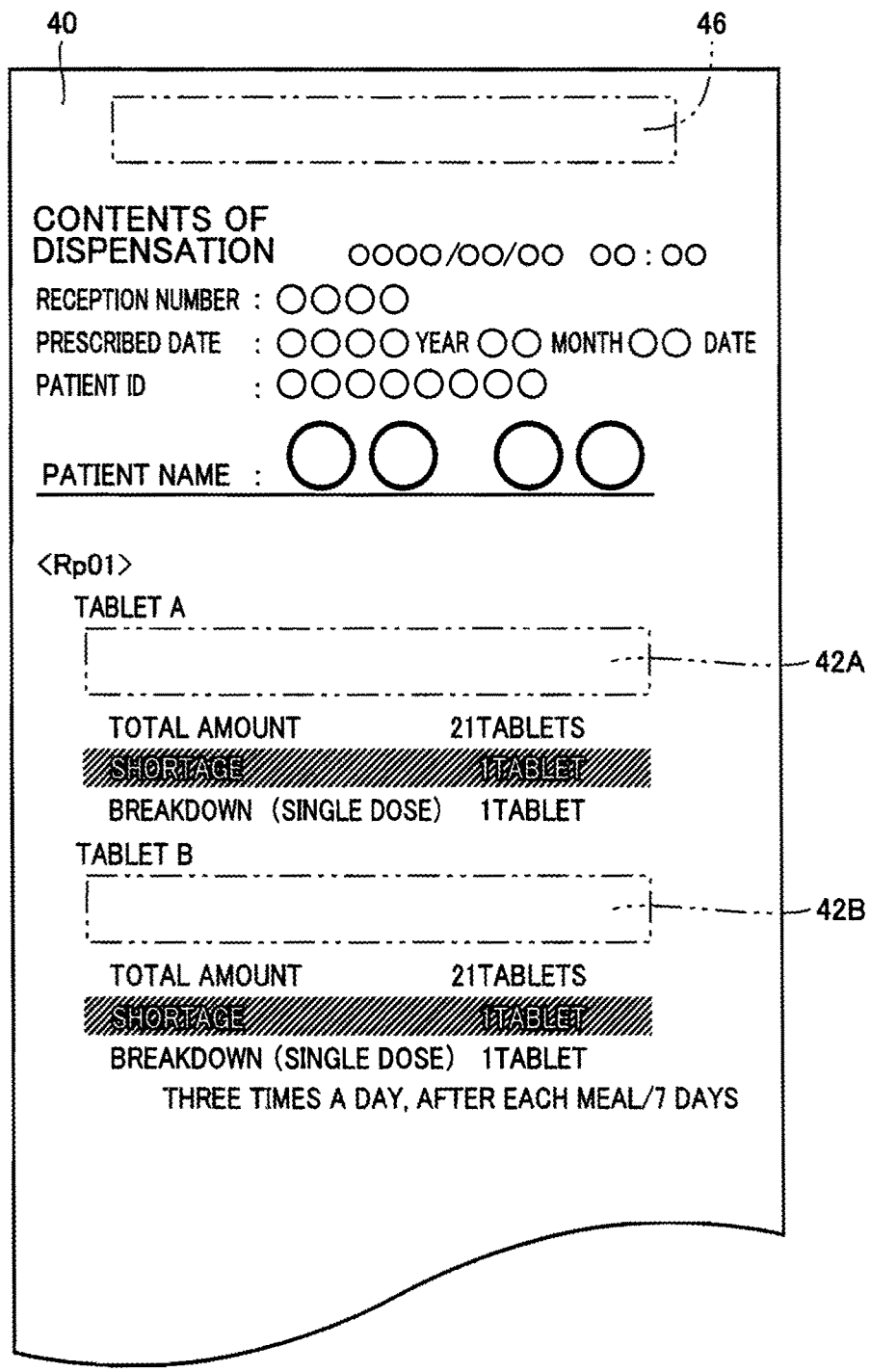
FIG. 7 is a schematic diagram illustrating a third example of the dispensation result slip output by the drug dispensing apparatus.

FIG. 7 is a schematic diagram illustrating a third example of dispensation result slip 40 output by drug dispensing apparatus 10. The print on dispensation result slip 40 shown in FIG. 7 indicates that there is a shortage of one tablet for tablets A, which are taken one tablet at a time. That is, although it was necessary to dispense a total of 21 tablets A according to the prescription, the number of tablets A housed in drug dispensing apparatus 10 was insufficient. Thus, dispensation result slip 40 indicates that 20 tablets A were dispensed from drug dispensing apparatus 10, with a shortage of one tablet A as a result of the dispensation.

The print on dispensation result slip 40 also indicates that there is a shortage of one tablet for tablets B, which are taken one tablet at a time. That is, although it was necessary to dispense a total of 21 tablets B according to the prescription, the number of tablets B housed in drug dispensing apparatus 10 was insufficient. Thus, the print on dispensation result slip 40 indicates that 20 tablets B were dispensed from drug dispensing apparatus 10, with a shortage of one tablet B as a result of the dispensation.

The drug code and the insufficient number of tablet A that were not dispensed are barcoded and printed on dispensation result slip 40 as bar code 42A. The drug code and the insufficient number of tablet B that were not dispensed are barcoded and printed on dispensation result slip 40 as bar code 42B. The supplementary information indicated with bar code 42 is read with mobile terminal 22 of picking inspection apparatus 20, and the worker collects the insufficient drugs by picking them from the pharmaceutical shelf based on the supplementary information.

Figure 8:
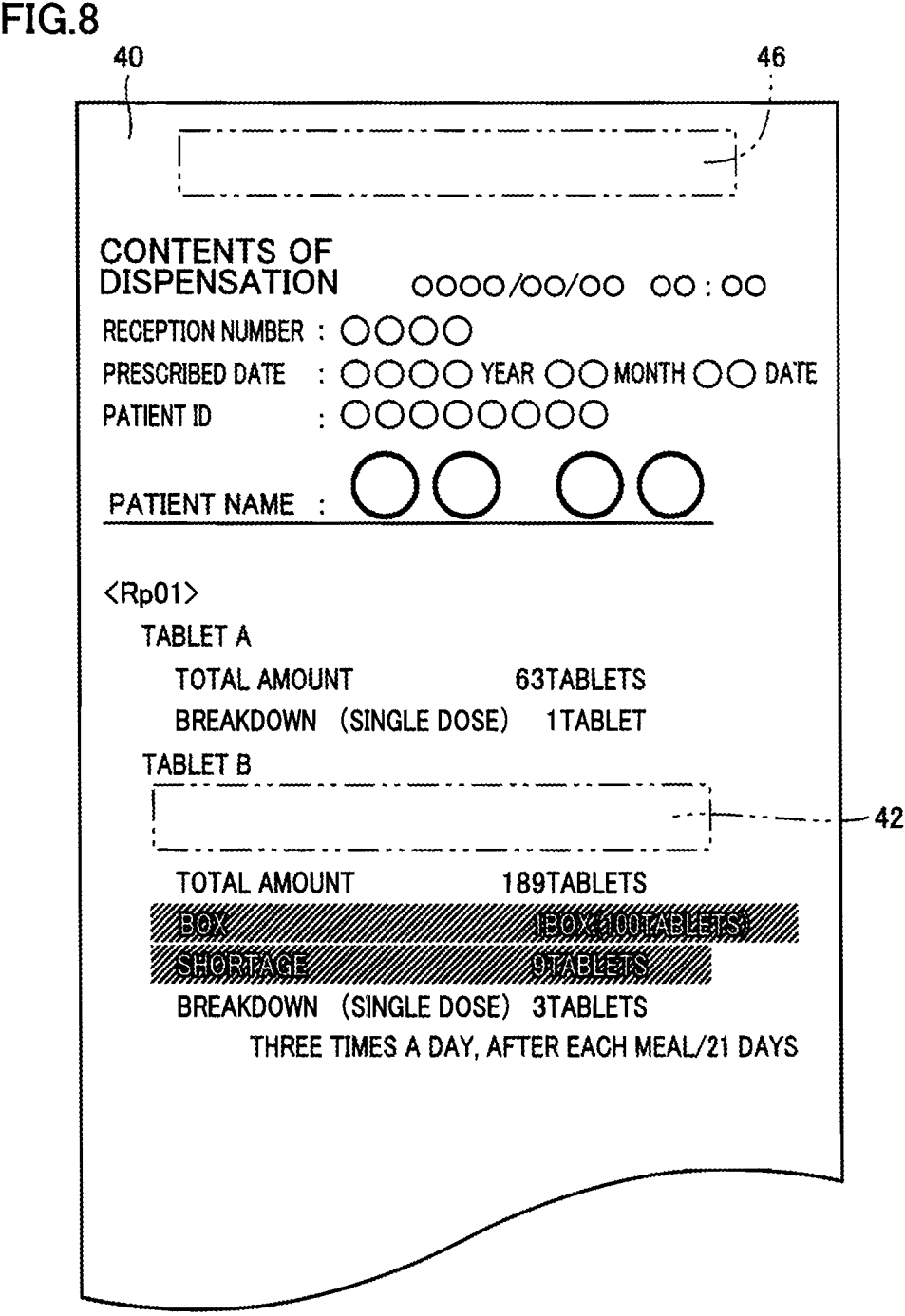
FIG. 8 is a schematic diagram illustrating a fourth example of the dispensation result slip output by the drug dispensing apparatus.

FIG. 8 is a schematic diagram illustrating a fourth example of dispensation result slip 40 output by drug dispensing apparatus 10. The print on dispensation result slip 40 shown in FIG. 8 indicates that a total of 63 tablets A, which are taken one tablet at a time, were dispensed. The required amount of tablets A were all dispensed from drug dispensing apparatus 10, and thus, the worker need not pick any additional tablet A.

The print on dispensation result slip 40, on the other hand, indicates that one box (100 tablets) of tablets B, which are taken three tablets at a time, were not dispensed, with a shortage of nine tablets for tablets B. That is, the amount of required tablets B in accordance with the prescription is equal to or more than the number of tablets B per box, and although drug dispensing apparatus 10 needed to dispense 89 tablets B, which is the remainder of the result of dividing the required number by the number of tablets per box, the number of tablets B housed in drug dispensing apparatus 10 was insufficient. Thus, the print on dispensation result slip 40 indicates that 80 tablets B were dispensed from drug dispensing apparatus 10, with a shortage of nine tablets B as a result of the dispensation.

The drug code and the insufficient number of tablets B that were not dispensed and need to be picked in box are barcoded and printed on dispensation result slip 40 as bar code 42. The supplementary information indicated with bar code 42 is read with mobile terminal 22 of picking inspection apparatus 20, and the worker collects the insufficient drugs by picking it from the pharmaceutical shelf based on the supplementary information.

Figure 9:
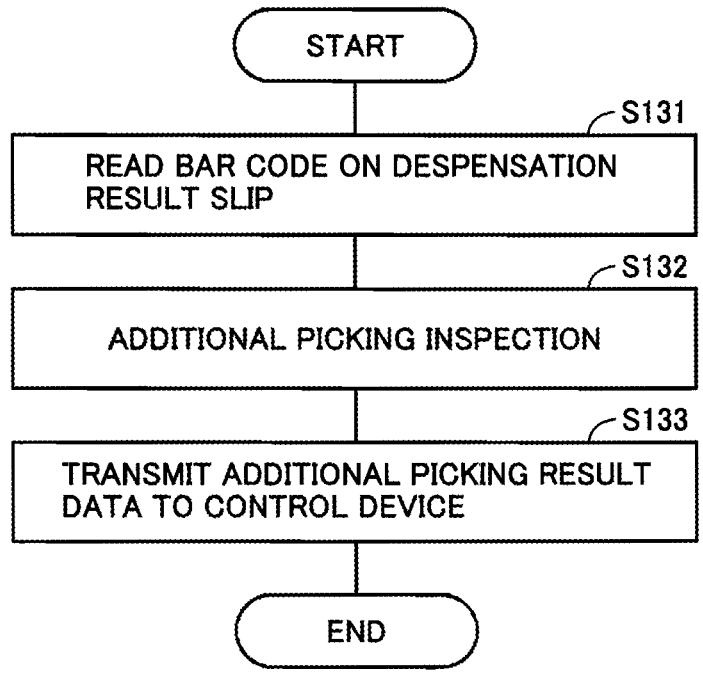
FIG. 9 is a flowchart illustrating the operation of the mobile terminal of the picking inspection apparatus when supplementary work by a worker is required.
Figure 10:
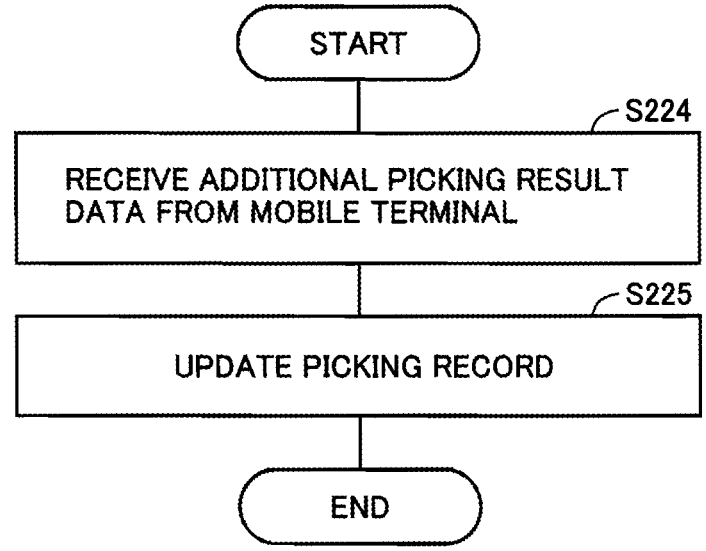
FIG. 10 is a flowchart illustrating the operation of the control device of the picking inspection apparatus when supplementary work by a worker is required.

FIG. 9 is a flowchart illustrating the operation of mobile terminal 22 of picking inspection apparatus 20 when supplementary work by a worker is required. FIG. 10 is a flowchart illustrating the operation of control device 24 of picking inspection apparatus 20 when supplementary work by a worker is required. When the worker needs to supplement a drug by conducting additional picking, as a result of the dispensation from drug dispensing apparatus 10, mobile terminal 22 and control device 24 of picking inspection apparatus 20 operate in accordance with the steps shown in FIGS. 9 and 10. With reference to FIGS. 9 and 10, the operation of control device 24 and mobile terminal 22 of picking inspection apparatus 20 when the supplementary work by the worker is required will be described in detail.

In step (S131) shown in FIG. 9, the worker who conducts additional picking reads bar code 42 printed on dispensation result slip 40 with mobile terminal 22. The worker checks the name and the quantity of the drug that needs to be supplemented, with reference to dispensation result slip 40 and the screen of mobile terminal 22. Then in step (S132), while conducting the additional picking, the worker conducts an additional picking inspection by reading the bar code provided for the drug that needs to be supplemented, with mobile terminal 22. After the completion of the additional picking inspection, mobile terminal 22 transmits the picking result data indicating the result of the additional picking inspection to control device 24 in step (S133).

In step (S224) shown in FIG. 10, control device 24 of picking inspection apparatus 20 receives the additional picking result data from mobile terminal 22. Control device 24 then in step (S225), updates the picking record stored in storage unit 26 in step (S25) based on the additional picking result data. The additional picking result data includes information on the supplementary drug additionally picked by the worker, which was included as a drug to be dispensed but was not actually dispensed from dispensing apparatus main body 12, and is stored in storage unit 26 of picking inspection apparatus 20.

As described above, in drug prescribing system 1 of this embodiment, the prescription data is transmitted from host computer 4 to drug dispensing apparatus 10 and picking inspection apparatus 20 simultaneously. This allows drug dispensing apparatus 10 to dispense drugs, and picking inspection apparatus 20 to conduct a picking inspection concurrently. Consequently, the time required to collect all the drugs can be reduced.

Picking inspection apparatus 20 receives an input of the supplementary information output by drug dispensing apparatus 10, and conducts a picking inspection for a drug that needs to be supplemented, based on the supplementary information. Thus, picking inspection apparatus 20 can conduct a picking inspection not only for a drug to be picked, but also for the drug that needs to be supplemented, which could not be dispensed with drug dispensing apparatus 10 or was not dispensed with drug dispensing apparatus 10 intentionally. Since picking inspection apparatus 20 can conduct picking inspections for all the drugs collected by picking twice in total, picking of a wrong drug by the worker can be reliably prevented.

The supplementary information is barcoded and printed on dispensation result slip 40 output by drug dispensing apparatus 10, and the bar code on dispensation result slip 40 is read through bar code reader 28 of mobile terminal 22. This allows the supplementary information to be transmitted from drug dispensing apparatus 10 to picking inspection apparatus 20. To transmit the supplementary information from drug dispensing apparatus 10 to picking inspection apparatus 20, bar code reader 28 originally provided for picking inspection apparatus 20 is used, and the supplementary information is transmitted via bar code 42. This eliminates the need to provide a separate communication means for transmitting the supplementary information, leading to a simplified configuration of drug prescribing system 1.

The result of dispensation from drug dispensing apparatus 10 is recorded in storage unit 16 of control device 14 of drug dispensing apparatus 10. The picking result data indicating the result of the picking inspection for the drug picked by the worker is recorded in storage unit 26 of control device 24 of picking inspection apparatus 20. Furthermore, when the supplementary work by the worker is required after the dispensation with drug dispensing apparatus 10, the additional picking result data is transmitted to control device 24 from mobile terminal 22 and recorded in storage unit 26. Control device 24 updates the picking record stored in storage unit 26 based on the additional picking inspection result. In this way, the dispensation record on the dispensation of drugs with drug dispensing apparatus 10 and the picking record on the picking inspections with picking inspection apparatus 20 can be accurately stored. By comparing the prescription data with the total of the dispensation record and the picking record, it is possible to more easily and reliably inspect whether the drugs prescribed in the prescription have been collected in predetermined quantities.

(Second Embodiment)

Figure 11:
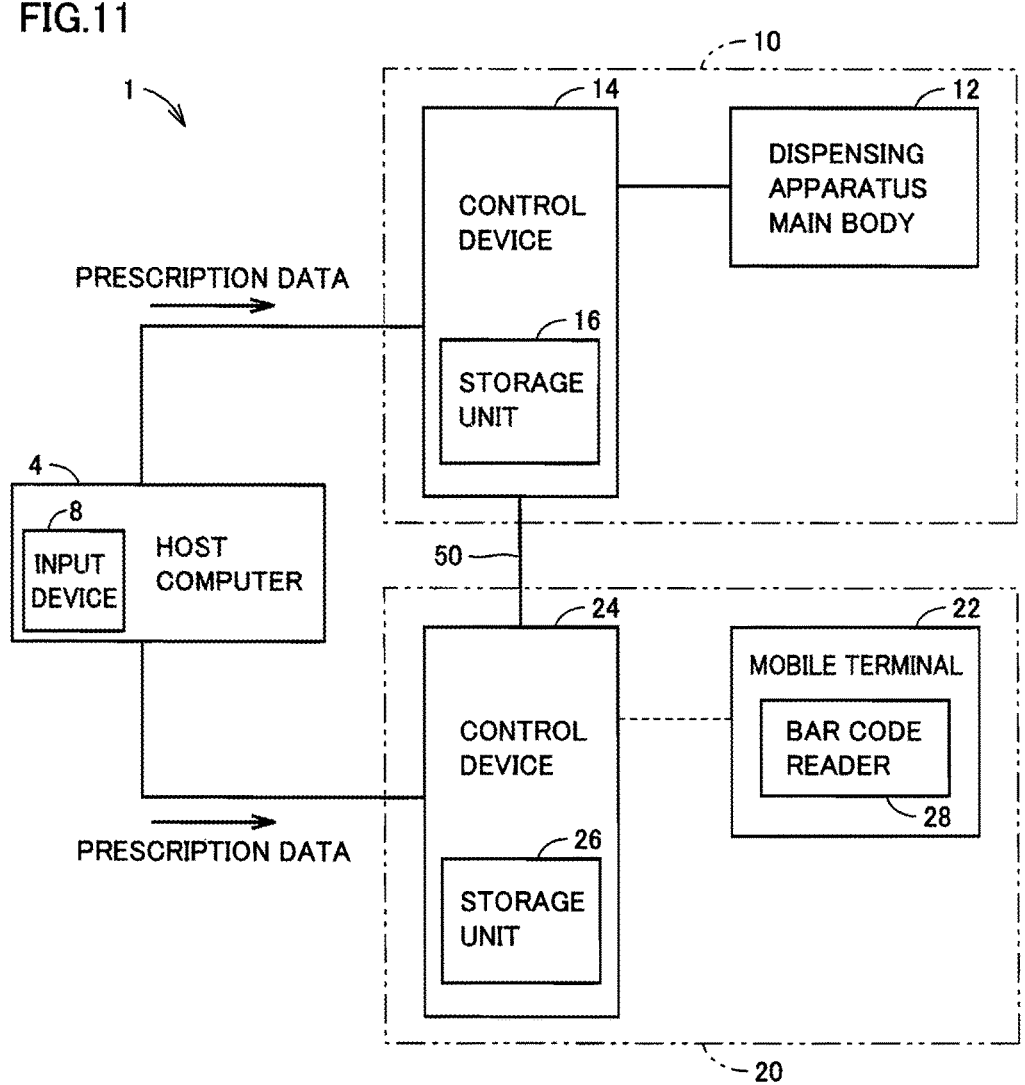
FIG. 11 is a block diagram illustrating the schematic configuration of a drug prescribing system according to a second embodiment.

FIG. 11 is a block diagram illustrating the schematic configuration of drug prescribing system 1 according to a second embodiment. Drug prescribing system 1 according to the second embodiment shown in FIG. 11 differs from that according to the first embodiment in that it includes wiring 50 directly connecting control device 14 of drug dispensing apparatus 10 and control device 24 of picking inspection apparatus 20.

When the supplementary work by the worker is required after the dispensation with drug dispensing apparatus 10, information on the name and the quantity of a drug that needs to be supplemented is transmitted via wiring 50 from control device 14 of drug dispensing apparatus 10 to control device 24 of picking inspection apparatus 20. Control device 24 transmits data on the drug that needs to be supplemented to mobile terminal 22 via wireless LAN. The worker checks the name and the quantity of the drug that needs to be supplemented, with reference to the screen of mobile terminal 22, and conducts additional picking, and also conducts an additional picking inspection.

The means for transmitting the information on a drug that was not dispensed from drug dispensing apparatus 10 and needs to be supplemented from drug dispensing apparatus 10 to picking inspection apparatus 20 is not limited to reading of bar code 42 printed on dispensation result slip 40, as described in the first embodiment. Drug prescribing system 1 may alternatively be configured such that via wiring 50 directly connecting control device 14 of drug dispensing apparatus 10 and control device 24 of picking inspection apparatus 20, the data on a drug that needs to be supplemented is automatically transmitted from control device 14 to control device 24.

In this case, it is unnecessary for the worker to read bar code 42 printed on dispensation result slip 40 with bar code reader 28. Consequently, the work that needs to be performed by the worker for collecting drugs in accordance with the prescription data can be reduced, allowing the work to become easier.

While embodiments of the present invention have been described as above, it should be understood that the embodiments disclosed herein are illustrative and non-restrictive in every respect. The scope of the present invention is defined by the terms of the claims, and is intended to include any modifications within the scope and meaning equivalent to the terms of the claims.

REFERENCE SIGNS LIST

1: drug prescribing system; 4: host computer; 8: input device; 10: drug dispensing apparatus; 12: dispensing apparatus main body; 14, 24: control device; 16, 26: storage unit; 18: printer; 20: picking inspection apparatus; 22: mobile terminal; 28: bar code reader; 40: dispensation result slip; 42, 42A, 42B, 46: bar code; 50: wiring.

The invention claimed is:

1. A drug dispensation and inspection system, comprising:
a host computer having a prescription data input device through which prescription data based on a prescription is input;
a drug dispensing apparatus in which drugs are housed in advance, and that dispenses a drug in accordance with said prescription data received from said host computer;
a picking inspection apparatus that conducts a picking inspection for drugs picked in accordance with said prescription data received from said host computer, said picking inspection apparatus having a bar code reader capable of reading a bar code, and said picking inspection apparatus conducting said picking inspection by reading a bar code provided for a drug through said bar code reader;
said drug dispensing apparatus capable of dispensing the drug and said picking inspection apparatus capable of conducting said picking inspection concurrently,
said drug dispensing apparatus analyzing, based on said prescription data received from said host computer, whether the drugs included in said prescription data are drugs to be dispensed with said drug dispensing apparatus or not, and dispensing the drugs to be dispensed among the drugs included in said prescription data, said picking inspection apparatus analyzing, based on said prescription data received from said host computer, whether the drugs included in said prescription data are drugs to be picked by a worker or not, instructing the worker to pick the drugs to be picked among the drugs included in said prescription data, and conducting said picking inspection by comparing the bar code that has been read through bar code reader during picking by the worker with the information on the drugs to be picked among the drugs included in said prescription data, said drug dispensing apparatus outputting supplementary information regarding a drug that is included as the drugs to be dispensed but that is not actually dispensed by said drug dispensing apparatus and thereby needs to be additionally picked by the worker, and said picking inspection apparatus receiving from said drug dispensing apparatus an input of said supplementary information, and conducting said picking inspection by comparing the bar code that has been read through bar code reader during additional picking by the worker with said supplementary information.

2. The drug dispensation and inspection system according to claim 1, wherein
said drug dispensing apparatus prints a dispensation result slip,
said supplementary information is barcoded and printed on said dispensation result slip, and
said bar code reader reads a bar code printed on said dispensation result slip, which causes said supplementary information to be transmitted from said drug dispensing apparatus to said picking inspection apparatus.

3. The drug dispensation and inspection system according to claim 1, further comprising:
a storage device that stores a dispensation record on dispensation of the drug with said drug dispensing apparatus, and a picking record on said picking inspection by said picking inspection apparatus, wherein
the drug additionally picked by the worker based on said supplementary information is included in said picking record, and not included in said dispensation record.

4. The drug dispensation and inspection system according to claim 2, further comprising:
a storage device that stores a dispensation record on dispensation of the drug with said drug dispensing apparatus, and a picking record on said picking inspection by said picking inspection apparatus, wherein
the drug additionally picked by the worker based on said supplementary information is included in said picking record, and not included in said dispensation record.

5. The drug dispensation and inspection system according to claim 1, wherein
said host computer is configured to simultaneously transmit said prescription data to said drug dispensing apparatus and to said picking inspection apparatus for reduced time of collection of drugs based on said prescription data.

6. The drug dispensation and inspection system according to claim 1, wherein
said drug dispensing apparatus outputs for said picking inspection apparatus said supplementary information by printing a dispensation result slip for said picking inspection apparatus having said supplementary information coded thereon or by transmitting said supplementary information electronically to said picking inspection apparatus.

7. The drug dispensation and inspection system according to claim 1, wherein
said picking inspection apparatus has a mobile terminal that is configured to acquire digital data of drugs taken by the worker during picking of drugs and a control device that receives said digital data from said mobile terminal.

* * * * *